United States Patent
Christensen

(10) Patent No.: US 7,318,920 B2
(45) Date of Patent: *Jan. 15, 2008

(54) LOW WATER ACTIVITY NUTRITIONAL PRODUCT HAVING BENEFICIAL MICROBIAL AND HIGH OIL CONTENT

(75) Inventor: Edwin H. Christensen, Coral Springs, FL (US)

(73) Assignee: Ez-Med Company, Pompano Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/968,407

(22) Filed: Oct. 19, 2004

(65) Prior Publication Data

US 2006/0067922 A1 Mar. 30, 2006

Related U.S. Application Data

(60) Provisional application No. 60/614,768, filed on Sep. 30, 2004, provisional application No. 60/613,325, filed on Sep. 27, 2004.

(51) Int. Cl.
*A01N 63/00* (2006.01)
(52) U.S. Cl. .................................................. 424/93.45
(58) Field of Classification Search ............. 424/93.45, 424/400; 426/61, 94
See application file for complete search history.

(56) References Cited

U.S. PATENT DOCUMENTS

| | | | |
|---|---|---|---|
| 3,567,819 A | 3/1971 | Leonia | |
| 3,615,652 A | 10/1971 | Burgess | |
| 4,025,624 A | 5/1977 | Alphin et al. | |
| 4,284,652 A | 8/1981 | Christensen | |
| 4,327,076 A | 4/1982 | Puglia et al. | |
| 4,643,894 A | 2/1987 | Porter et al. | |
| 4,643,908 A | 2/1987 | Sawhill | |
| 4,671,953 A | 6/1987 | Stanley et al. | |
| 4,710,387 A | 12/1987 | Uiterwaal et al. | |
| 4,795,643 A | 1/1989 | Seth | |
| 4,882,153 A | 11/1989 | Yang et al. | |
| 4,935,243 A | 6/1990 | Borkan et al. | |
| 5,262,167 A | 11/1993 | Vegesna et al. | |
| 5,296,209 A | 3/1994 | Simone et al. | |
| 5,456,922 A | 10/1995 | Cady et al. | |
| 5,512,308 A | 4/1996 | Mishkin et al. | |
| 5,607,697 A * | 3/1997 | Alkire et al. ............... 424/498 |
| 5,637,313 A | 6/1997 | Chau et al. | |
| 5,643,603 A | 7/1997 | Bottenberg et al. | |
| 5,718,770 A | 2/1998 | Shah et al. | |
| 6,387,381 B2 | 5/2002 | Christensen | |
| 6,537,666 B1 | 3/2003 | Bronshtein | |
| 6,716,448 B2 | 4/2004 | Huber et al. | |
| 6,723,358 B1 * | 4/2004 | van Lengerich ............. 426/94 |
| 2003/0198668 A1 * | 10/2003 | Abbas et al. ............... 424/452 |
| 2007/0122397 A1 | 5/2007 | Sanguansri et al. | |

FOREIGN PATENT DOCUMENTS

WO WO 9734615 A1 * 9/1997

OTHER PUBLICATIONS

Mechanical strength testing machines: some information on tablet hardness testing, see at the web- http://www.engsys.co.uk. pp. 1-5, Jan. 21, 2006.*
Davis GS & Anderson KE, "The efects of feeding the direct-fed microbial, Primalac, on growth parameters and egg production in Single Comb White Leghorn hens", Reserach Notes, Poultry Science, 2002, 81: 755-759. entire document.*
New Protection for Health-Promoting Probiotics, *Preventive Health*, Jun. 2005, Crittenden, Sanguansri, Augustin, Weerakkoody [highlighted *by* American Society for Microbiology (AMS) in *Microbe*, May 2006).
Associated Content, Internet Article, *Health Benefits of Probiotics—Why You Need Them*, 2007; Author (Content Producer); thereviewer; Website: Associated Content: The People's Media Company, Apr. 30, 2007
Probiotics-Good Bacteria Meet Functional Foods, Author Gregor Reid; *Functional Ingredients Magazine*; Nov. 2002.
Probiotics Update: the latest word on these friendly bacteria; Author Sarah Gregory; Article in *Better Nutrition*, Apr. 24, 2004.
ConsumerLab.com [website] *Product Review: Probiotic Supplements and Foods (Including Lactobacillus acidophillus and Bifidobacterium) ConsumerLab.com, LLC 2003.*
Search Results, pp. 2-110, Oct. 12, 2007.
Office Action of May 25, 2007.

* cited by examiner

*Primary Examiner*—Sandra E. Saucier
*Assistant Examiner*—Satyendra K. Singh
(74) *Attorney, Agent, or Firm*—Welsh & Katz, Ltd.

(57) ABSTRACT

The present invention relates to a composition for the oral administration of beneficial microorganisms in a discrete dosage form, comprising about 10% to about 50% by weight of a starch component, about 25% to about 50% by weight of a sugar component, about 0-20% of a humectant component, and about 5% to about 25% by weight of water. The composition has a soft and chewy texture and water activity of about 0.60 to about 0.75.

9 Claims, No Drawings

LOW WATER ACTIVITY NUTRITIONAL PRODUCT HAVING BENEFICIAL MICROBIAL AND HIGH OIL CONTENT

CROSS REFERENCE TO RELATED APPLICATIONS

This application claims the benefit of priority to U.S. Provisional Application No. 60/613,325 entitled LOW WATER ACTIVITY NUTRITIONAL PRODUCT HAVING BENEFICIAL MICROBAL AND HIGH OIL CONTENTS filed on Sep. 27, 2004 by Edwin H. Christensen, and U.S. Provisional Application No. 60/614,768 entitled LOW WATER ACTIVITY NUTRITIONAL PRODUCT HAVING BENEFICIAL MICROBAL AND HIGH OIL CONTENTS filed on Sep. 30, 2004 by Edwin H. Christensen.

FIELD OF THE INVENTION

This application is directed to a means for delivering nutrition containing either or both of a probiotic or substantial oil content to humans or animals and more specifically, the control of the water activity of a food product matrix for use in the incorporation of either or both of a probiotic or substantial oil content, as well as pharmaceutically useful substances, such as ivermectin and pyrantel.

BACKGROUND OF THE INVENTION

Beyond ordinary nutritional value, food can be supplemented with pharmaceutical or specialized nutritional additives to improve the health of a consuming human or animal. These additives can be intended to either be a regular e.g. daily part of a diet, or consumed intermittently, e.g. weekly or monthly.

One class of additive, probiotics, are live microbial organisms that beneficially affect animal or human hosts. Some known beneficial effects include improvement of the microbial balance of the intestinal microflora that aid digestion in higher animals. An example of a beneficial effect of probiotics is their use against specific groups of organisms, resulting in a decrease in numbers, by an effect on their metabolism or by stimulation of immunity. The introduction of a probiotic organism can suppress counts of an undesired organism by producing antibacterial compounds, by competing for nutrients or adhesion sites. Further, probiotics may alter microbial metabolism by increasing or decreasing enzyme activity or they may stimulate the immune system by increasing antibody levels or increasing macrophage activity.

While fatty acids, or lipids, can be provided in a variety of forms, some are more important than others. There are essential fatty acids that are not manufacturable by humans or some animals. Essential fatty acids fall into two groups: omega-3 and omega-6. The 3 and 6 refer to the first carbon double bond position on the fatty acid chain. All essential fatty acids are polyunsaturated, so the 3 and the 6 mean that the first double bond is either 3 or 6 carbons in from the end. Essential fatty acids include omega-6 fatty acids linoleic acid, arachidonic acid, gamma linolenic acid, dihomogamma linolenic acid, and the omega-3 fatty acids alpha linolenic acid, eicosapentaenoic acid, and docosahexaenoic acid.

Omega-6 fatty acids are common: corn oil, sunflower oil and soybean oil all contain them. Omega-3 fatty acids are less common. Flax seeds, pumpkin seeds and walnuts are high in omega-3 fatty acids, as are salmon, trout and tuna. Current thinking is that these two fats need to be balanced in the diet at a ratio like 1-to-1 or 2-to-1, rather than the normal 20-to-1 ratio seen in most Western diets. Fatty fish like mackerel, lake trout, herring, sardines, albacore tuna and salmon are high in two kinds of omega-3 fatty acids, eicosapentaenoic acid and docosahexaenoic acid. Therefore, one way to achieve a proper balance is to supplement the diet with omega-3 fatty acid containing oils such as fish oils.

Fish oils can help humans to ameliorate or reverse atherosclerosis, angina, heart attack, congestive heart failure, arrhythmias, stroke, and peripheral vascular disease and may have other health benefits by helping to maintain the elasticity of artery walls, prevent blood clotting, reduce blood pressure and stabilize heart rhythm. Fish oils can also help animals maintain a healthy skin or coat.

Further, even simple mineral oils can aid the health of animals. For example, mineral oils can aid the passage of hairballs in cats through their digestive tracts.

Pharmaceutical and nutriceutical products intended for oral administration are typically provided in tablet, capsule, pill, lozenges and caplet form. These products are swallowed whole or chewed in the mouth for delivery of the active ingredient into the alimentary system of a body. Such oral delivery systems are sometimes made chewable to ease drug administration in pediatric and geriatric patients who may be uncooperative or particular about the form of nourishment they take. Concerns with ease of administration are also amplified when dealing with pets and other animals whose cooperation may be difficult to obtain. Accordingly, a food matrix that can not only contain pharmaceutical or nutriceutical products but also have acceptable appearance, texture, hardness, and other indicia of acceptability such as smell and taste are desirable.

In order to provide a food with a long shelf life, it is also desirable to regulate the water activity ($a_w$) of a food. The water activity of a food is the ratio between the vapor pressure of the food itself, when in a completely undisturbed balance with the surrounding air media, and the vapor pressure of distilled water under identical conditions. A water activity of 0.80 means the vapor pressure is 80 percent of that of pure water. The water activity increases with temperature. The moisture condition of a product can be measured as the equilibrium relative humidity (ERH) expressed in percentage or as the water activity expressed as a decimal.

Most foods have a water activity above 0.95 and that will provide sufficient moisture to support the growth of bacteria, yeasts, and mold. The amount of available moisture can be reduced to a point which will inhibit the growth of the organisms. If the water activity of food is controlled to 0.85 or less in the finished product, it is not subject to the regulations of 21 CFR Parts 108, 113, and 114.

Water activity therefore affects food stability and therefore it must be brought to a suitable level at the conclusion of production and maintained within an acceptable range of activity values during storage.

As a result, several approaches have been utilized in the prior art in formulating oral delivery systems, including gums and candy bases. The use of such delivery systems is limited by the reaction of the active ingredient, whether it be pharmaceutical, nutriceutical or other ingredients, to the existence of water in the system, which can negatively impact shelf life, especially in the case of live probiotic material, which may undesirably multiply in the presence of moisture.

Accordingly, a food matrix that can deliver probiotic ingredients and contain high levels of oils while maintaining a low water activity level and a long shelf life are desirable to provide pharmaceutical and nutritional contributions to the health of animals.

SUMMARY OF THE INVENTION

The present invention relates to nutritional compositions formulated to provide beneficial microorganisms and health beneficial oils. A composition for oral administration of the beneficial microorganisms in a discrete dosage form includes about 0.1% to about 30% of those microorganisms by weight in a product. The product comprises about 10% to about 50% by weight of a starch component, about 25% to about 50% by weight of a sugar component, about 0-20% of a humectant component, and about 5% to about 25% by weight of water. The composition has a soft and chewy texture and water activity of about 0.60 to about 0.75, and preferably about 0.65.

In an exemplary embodiment of the present invention, the composition has a water content of about 10%.

In another exemplary composition the humectant is a polyhydric alcohol, and the humectant content is about 9% to about 11% by weight of product.

In a further embodiment of the invention, the composition has a starch component of about 25% to about 35% by weight.

In yet another embodiment, the composition has a water activity between about 0.60 and 0.75, and preferably about 0.65.

In another embodiment of the present invention, a composition for the oral administration of oils or fats in a discrete dosage form has the oil or fat included in a product at about 5% to about 25% by weight of product. The product comprises about 10% to about 50% by weight of a starch component, about 10% to about 50% by weight of a sugar component, about 0-10% by weight of a humectant component, about 0.01-0.5% by weight emulsifier, and about 5% to about 25% by weight water. The composition has a soft and chewy texture and water activity of about 0.65.

The exemplary oil containing composition can further have about 1% to about 7% by weight probiotics. Further, the oil may be mineral oil or fish oil.

The invention also contemplates a method of making a matrix and additive mixture for use in an oral administration of a fat or oil nutritional component. The method can begin by combining the dry ingredients, including at least a starch component, sugar component and humectant. Water can then be added to the dry ingredients to form a wet mix. Separately, emulsifier can be combined with the oil or fat to form a pre-emulsion. The pre-emulsion can then be mixed with the wet mix. The relative amounts of humectant and water are adjusted to control the water activity of said admixture to adjust the level of moisture in the matrix to be between about 0.65 and provide a non-greasy product.

The benefits of the present invention include providing a product having a low water activity that can provide beneficial microorganisms to animals as well as a high oil content of an oil that will be nutritious or have health benefits for an animal.

DESCRIPTION OF THE PREFERRED EMBODIMENTS

By the subject invention, a soft chewable nutrition product is provided that can be used to provide a controlled dose of beneficial microorganisms. The product can be cut, formed, or extruded into any shape, such as in a tablet form, a cylindrical form, a nugget form, or even fanciful shapes such as fish or stars, and may contain one or more active ingredients. The active ingredients are incorporated into the matrix which is described in further detail below and which includes a starch component, a sugar component, a humectant component, water, and optionally, a fat or oil component. The product may also have other ingredients such as extenders, bulking agents, preservatives, emulsifiers, flavorings, and other food additives known to those of ordinary skill in the art such as, but not limited to, acidulants, antioxidants, dietary fiber, firming agents, flavor enhancers and lubricants. A probiotic active ingredient can also then be incorporated into the matrix. After mixing these ingredients, the product may then be formed into an appropriate shape.

The relative proportions of a probiotic component, not listing an optional oil component, of the present invention are listed in Table 1

TABLE 1

| Component | Preferred | More Preferred | Most Preferred |
| --- | --- | --- | --- |
| Starch Component | 10-50% | 15-40% | 25-35% |
| Sugar Component | 25-50% | 25-40% | 2-37% |
| Humectant | 0-20% | 5-15% | 9-11% |
| Water | 5-20% | 10-15% | 9-13% |
| Extender/Bulking Agent | 0-50% | 3-35% | 6-26% |
| Microbal/Probiotic Component | 0.1-30% | 1-7% | 2-6% |

Generally speaking, the starch component of the matrix comprises 10 to 50 percent by weight of the matrix. More particularly, the starch component of the matrix comprises 15 to 40 percent by weight of the matrix, with 25-35% being a most particular embodiment.

While starch for use in the matrix can be of any suitable type, it is most preferred that at least part of the starch in the matrix be a highly derivatized or pregelatinized starch. Where components are to be used in a product that will not withstand heating, it is preferred that all of the starch be pregelatinized. If a highly derivatized starch is present in the matrix, it should be present in an amount of about 50 percent by weight of the total starch and the balance of the starch being non-derivatized. More preferably, about 20-40 percent by weight of the total matrix and about 45% of the total starch should be the derivatized starch. An example of preferred pregelatinized starches are those provided by A. E. Staley. As will be appreciated by those of ordinary skill in the art, the selection of starches or the use of mixtures of starches may be used to achieve desired hardness properties.

Hardness can be measured using a Chatillon Digital Force Gauge (DFIS-50) using an inverse wedge tip (appearing as if a wedge has been removed from the center of the tip, leaving two edges at the sides, and a wedge-shaped gap in the center). The Chatillon Digital Force Gauge (DFIS-50) is turned on, and typically measurements are averaged over a number of samples, typically 6. The UNITS button on the front of the Chatillon is pressed until lbs. is displayed, and The PEAK button on the front of the Chatillon is pressed until "peak" and "c" for compression is displayed. A solid cylindrical product piece is placed on the round flat metal disk under the Chatillon tip facing lengthwise perpendicular to the front of the Chatillon device. Then an arm is moved slowly backwards so that the tip lowers and is forced through the sample piece. The motion should take approximately 1 second. Going too fast or too slow will can give inaccurate readings. The force in lbs. is then recorded from the face of the Chatillon and logged. After each measurement, the ZERO button is pressed to reset the peak value back to zero.

Specifically, hardnesses of between 2 and 50 pounds measured on given the equipment and technique above are desirable to provide nutrition of potentially uncooperative subjects, such as animals so as to minimize resistance to intake of the nutrition. More specifically, the hardness can be between about 6 and 33 pounds.

Other amylaceous ingredients may be used in combination with the derivatized starch or alone, provided the starch limits are not exceeded. The amylaceous ingredients can be gelatinized or cooked before or during the forming step to achieve the desired matrix characteristics. If pregelatinized starch is used, it may be possible to prepare the product of the subject invention or perform the method of the subject invention without heating or cooking of any sort. However, if ungelatinized (ungelled) or uncooked starch is used, the matrix must be cooked sufficiently to gel or cook the starch to reach the desired content.

Starches that can serve as a base starch for derivatization include regular corn, waxy corn, potato, tapioca, rice, etc. Such types of derivatizing agents for the starch include but are not limited to ethylene oxide, propylene oxide, acetic anhydride, and succinic anhydride, and other food approved esters or ethers, introducing such chemicals alone or in combination with one another. Prior crosslinking of the starch may or may not be necessary based on the pH of the system and the temperature used to form the product.

By "amylaceous ingredients" is also meant those foodstuffs sometimes termed extenders or bulking agents containing a substantial amount of starch and/or starch-like material. Examples of amylaceous ingredients are cereal grains and meals or flours obtained upon grinding cereal grains such as corn, oats, wheat, milo, barley, rice, and the various milling by-products of these cereal grains such as wheat feed flour, wheat middlings, mixed feed, wheat shorts, wheat red dog, oat groats, hominy feed, rice bran, and other such material. Also included as sources of amylaceous ingredients are the tuberous food stuffs such as potatoes, tapioca, and the like.

Generally speaking, the sugar component of the matrix comprises 25 to 50 percent by weight of the matrix. More particularly, the sugar component of the matrix comprises 25 to 40 percent by weight of the matrix, with 23-37% being a most particular embodiment.

The sugar component can be employed in a dry or crystalline condition or can be an aqueous syrup having a sugar concentration of from 50 to about 95, preferably from 70 to about 80, weight percent. The sugar used can be lactose, sucrose, fructose, glucose, or maltose, depending on the particular application and price or availability of a particular sugar. Examples of various well established sources of these sugars are, corn syrup solids, malt syrup, hydrolyzed corn starch, hydrol (syrup from glucose manufacturing operations), raw and refined cane and beet sugars, etc.

The humectant can be a polyhydric alcohol component of the matrix can be selected from glycerol, sorbitol, propylene glycol, 1,3-butanediol, and mixtures thereof with each other or other humectant known to those of ordinary skill in the art. Generally the humectant comprises about 0 to about 20 percent by weight of the matrix. More specifically, the humectant comprises about 5 to about 15 percent by weight of the matrix, or most specifically 9-11% of the matrix.

Water is added to the other ingredients to form the matrix in the amount of at least 5 percent by weight of the ingredients of the matrix. More specifically, water is generally added in the matrix about 5 percent to about 20 percent by weight of the ingredients of the matrix.

While water must initially be added in the amount of at least 5 percent by weight of the ingredients of the matrix, when the matrix is used in a food product, the moisture of the food product must be adjusted in accordance with all the ingredients. The desired moisture content may be achieved in any suitable fashion. Normal processing may produce the moisture content desired. A standard drying step is optional and may be used if necessary.

Generally speaking, the probiotic component of the final product comprises from about 0.1 to about 30% percent by weight of the matrix. More particularly, the probiotic component of the matrix comprises from about 1 to about 7 percent by weight of the matrix, with about 2 percent to about 6 percent being a most particular embodiment.

The beneficial microbial, or probiotic ingredient is preferably a non-refrigerated type of live bacterial culture. One example is a lactobacillus/streptococcus bacterial culture. A suitable culture is sold under the identification of Primalac 454 F/G by Star Labs/Forage Research of Clarksdale, Mo., which contains lactobacillus acidophilus, lactobacillus casei, bifidobacterium thermophilum, and enterococcus faecium dehydrated fermentation products. Suitable cultures may contain not only dehydrated fermentation products, but other additives present to give the culture appropriate handling characteristics. For example, beyond the culture fermentation products themselves, the recited Primalac product also contains rice hulls, calcium carbonate, and vegetable oil. However, suitable probiotic materials will activate and grow under the influence of moisture. Preferably, such the probiotic component ingredients are of a dried variety, though fluid culture components may also be used.

Optionally, the probiotic ingredient may be present with other additional active ingredients, such as ivermectin and pyrantel. Ivermectin and pyrantel provide the additional health benefits of heartworm or pinworm protection. Specifically, ivermectin can be provided in an amount of about 6 micrograms of ivermectin per kilogram of body weight and pyrantel can be provided in an amount of 5 milligrams per kilogram of body weight to prevent heartworm disease. In an exemplary form, intended for a patient having a body weight of about 25 kilograms, a 2.5 gram tablet can contain 0.006% ivermectin, or 0.15 milligrams per tablet of ivermectin, and 4.6% pyrantel, or 115 milligrams of pyrantel per tablet. Other formulations can be made for patients with higher or lower body weights.

A relatively dry product as exemplified in Table 1 can also have preservatives, optionally present at a level of about 0.0 to about 0.5%, an emulsifier to aid processing, optionally present at a level of about 0.0 to 0.2%, and flavoring, optionally present at a level of about 0.0 to about 4.0%.

The high oil content product of the present invention, which may or may not contain the probiotic component, ivermectin, or pyrantel discussed earlier, can have proportions that are listed in Table 2. If the optional probiotic component is present, it can be added in the same percentages as present in the dry, non-oily product detailed above. The types of ingredients that are suitable for practice of the high oil content embodiment are the same as for the probiotic product.

TABLE 2

| Component | Preferred | More Preferred | Most Preferred |
|---|---|---|---|
| Starch Component | 10-50% | 15-35% | 20-26% |
| Fat or Oil Component | 4-25% | 8-22% | 10-20% |
| Sugar Component | 10-50% | 15-30% | 18-25% |
| Humectant | 0-10% | 1-8% | 2-5% |
| Water | 5-25% | 5-20% | 5-15% |
| Extender/Bulking Agent | 0-50% | 10-30% | 14-22% |

As indicated in Table 2, a product of the present invention can have a oil or fat component. The fat component of the matrix can be about 4 to about 25% by weight of the matrix. More specifically, the fat component of the matrix is about 8 to about 22 percent by weight of the matrix, with the most specific product having about 10-20% oil. The selection of the oil or oils to comprise the oil component can either be done to complement other elements of an intended diet, or provide a balanced source of nutrition in a single product, or provide non-nutritive benefits, such as hairball management in cats, that can have important health and well-being impacts.

The fat or oil component of the matrix can be fat or oil of animal, vegetable or mineral origin, and may be either solid or liquid at room temperature. Typical animal fats or oils are fish oil, chicken fat, tallow, choice white grease, prime steam lard and mixtures thereof. Other animal fats are also suitable for use in the matrix. Vegetable fats or oils are derived from corn, soy, cottonseed, peanut, flax, rapeseed, sunflower, other oil bearing vegetable seeds, and mixtures thereof. Mineral oils may be obtained from petroleum processed petroleum. Additionally, a mixture of animal or vegetable oils or fats is suitable for use in the matrix. While not wishing to be bound by theory, it is believed that an oil component provides encapsulation for probiotics present, aiding in isolating the probiotic ingredients from water that could lead to undesirable growth of the microorganisms.

To form the matrix, the appropriate elements to the formula, including, but not limited to the starch system, humectant, sugar component and water, are mixed with equipment known to those of ordinary skill in the art. Examples of such equipment can include, but are not limited to, a Hobart mixer, a Day mixer, or even an extruder, such as a screw extruder for permitting addition of ingredients at different points along the barrel. The preferred probiotic ingredients recited above should be handled at temperatures not to exceed about 190° F., and desirably at room temperature (e.g. between 68° F. or 20° C. and 77° F. or 25° C.). One approach to achieving low temperatures is to introduce the water to be mixed with the other ingredients in the form of ice. In general, the matrix formed has a water activity of 0.60 to 0.75 after a period of about 3 days, and will not foment the growth of the probiotic ingredient in storage, or sustain invasion by adventitious organisms such as molds or fungi that may be encountered during storage.

The method can begin by combining the dry ingredients, including at least a starch component, sugar component and humectant. Water can then be added to the dry ingredients to form a wet mix, or first wet intermediate. Separately, emulsifier can be combined with the oil or fat to form a pre-emulsion. The pre-emulsion can then be mixed with the wet mix. If a non-greasy product is desired, the oil component and emulsifier should form a homogenous pre-emulsion prior to incorporating it into a wet mix to produce a dough. A non-greasy product will not have a shiny appearance, and will not shed noticeable amounts of oil onto bare hands when handled.

Other mixing apparatus, such as a sigma mixer, swept wall heat exchanger or the like may be used. If a natural coloration is desired in the final product pregelled starches are used to form the matrix. The use of these pregelled starches avoids high cooking temperatures which would destroy the desired natural coloration and/or active ingredient. If natural coloration active temperature sensitivity is not a problem, it is possible to use a cooked or ungelatinized starch to form the matrix and cook or gel the starch as the process is carried out. The incorporation of a derivatized starch in the product more clearly guarantees the softness of the product for a longer period of time. Softness is also provided by the fats and oils in addition to the use of softer starches. In this fashion a suitable matrix is provided for use with a wide variety of active ingredients.

Having fully described the invention, the following examples are presented to illustrate the invention without limitation thereof. In these examples all parts percentages are by weight unless otherwise specified.

EXAMPLE 1

| INGREDIENT | | A | B | C | D | E |
|---|---|---|---|---|---|---|
| Probiotic Component | | 2.0 | 2.0 | 2.0 | 2.0 | 2.0 |
| | Primalac 454 | 2.0 | 2.0 | 2.0 | 2.0 | 2.0 |
| Starch Component | | 28.0 | 32.0 | 26.0 | 27.0 | 32.0 |
| | Pregel Corn Starch (Staley Mira Sperse 2000) (softer) | 8.0 | 8.0 | 6.0 | 6.0 | 8.0 |
| | Pregel Starch (Staley Mir-Gel 463) (harder) | 20.0 | 24.0 | 20.0 | 21.0 | 24.0 |
| Sugar Component | | 24.0 | 31.0 | 23.0 | 30.0 | 37.0 |
| | Dextrose | 8.0 | 12.0 | 8.0 | 12.0 | 18.0 |
| | Sucrose | 9.0 | 12.0 | 9.0 | 12.0 | 12.0 |
| | Corn Syrup | 7.0 | 7.0 | 6.0 | 6.0 | 7.0 |
| Humectant | | 11.0 | 11.0 | 9.0 | 9.0 | 11.0 |
| | Sorbitol | 11.0 | 11.0 | 9.0 | 9.0 | 11.0 |
| Extender/ Bulking Agent | | 23.6 | 12.6 | 25.7 | 17.7 | 6.6 |
| | Rice Bran | 23.6 | 12.6 | 15.7 | 7.7 | 6.6 |

-continued

| INGREDIENT | | A | B | C | D | E |
|---|---|---|---|---|---|---|
| | Brewer's Yeast | | | 10.0 | 10.0 | |
| Preservative | | 0.3 | 0.3 | 0.3 | 0.3 | 0.3 |
| | Sorbic Acid | 0.2 | 0.2 | 0.2 | 0.2 | 0.2 |
| | Sodium Benzoate | 0.1 | 0.1 | 0.1 | 0.1 | 0.1 |
| Lubricant | | 0.1 | 0.1 | 0.0 | 0.0 | 0.1 |
| | Lecithin Ultralec F | 0.1 | 0.1 | | | 0.1 |
| Water | | 9.0 | 9.0 | 13.0 | 13.0 | 9.0 |
| Flavors | | 2.0 | 2.0 | 1.0 | 1.0 | 2.0 |
| | Meat Flavor | 2.0 | 2.0 | 1.0 | 1.0 | 2.0 |
| Water Activity | | 0.648 @25.1 °C. | 0.680 @25.1 °C. | 0.659 @25.1 °C. | 0.685 @25.1 °C. | 0.642 @25.2 °C. |
| Colony Forming Units per gram | | | | | | |
| | first test (weeks after manufacturing) | $4.90 \times 10^6$ (5) | $9.73 \times 10^4$ (5) | $1.12 \times 10^5$ (5) | $2.73 \times 10^4$ (5) | $1.82 \times 10^5$ (3) |
| | second test (weeks after manufacturing) | $4.80 \times 10^4$ (9) | | $6.42 \times 10^3$ (9) | | $8.16 \times 10^3$ (7) |

The above ingredients are mixed at room temperature and formed into coin shapes and cylindrical shapes using a ROBOT 500 continuous automatic vacuum sausage filling machine from VERMAG Machinen und Anlagenbau GmbH, obtainable through Robert Reiser & Co. of Canton, Mass. The product has a dry non-greasy appearance, with no shine or wetness visible on the surface of the product. The samples had a hardness of about 33 lbs, based on the measurement system above using the digital force gauge.

EXAMPLE 2

| INGREDIENT | | F | G | H | I | J | K |
|---|---|---|---|---|---|---|---|
| Oil Component | | 20.0 | 20.0 | 20.0 | 10.0 | 20.0 | 20.0 |
| | Mineral Oil | 20.0 | 20.0 | 20.0 | 10.0 | 20.0 | 20.0 |
| Starch Component | | 26.0 | 22.0 | 20.0 | 22.0 | 24.0 | 24.0 |
| | Regular Corn Starch (Staley Mira Sperse 2000) | 6.0 | 2.0 | 0 | 6.0 | 4.0 | 4.0 |
| | Pregel Starch (Staley Mir-Gel 463) | 20.0 | 20.0 | 20 | 16.0 | 20.0 | 20.0 |
| Sugar Component | | 25.0 | 18.0 | 18.0 | 18.6 | 18.0 | 18.0 |
| | Dextrose | 10.0 | 18.0 | 18.0 | | 18.0 | 18.0 |
| | Sucrose | 7.0 | | | 15.6 | | |
| | Corn Syrup | 8.0 | 0.0 | 0.0 | 3.0 | 0.0 | |
| Humectant | | 5.0 | 2.0 | 4.0 | 5.0 | 0.0 | 0.0 |
| | Sorbitol | 5.0 | 2.0 | 4.0 | 5.0 | 0.0 | 0.0 |
| Extender/Bulking Agent | | 14.0 | 20.0 | 20.0 | 22.0 | 20.0 | 20.0 |
| | Rice Bran | 14.0 | 13.0 | 13.0 | 15.0 | 13.0 | 13.0 |
| | Brewer's Yeast Cheese Powder | | 7.0 | 7.0 | 7.0 | 7.0 | 7.0 |
| Preservative | | 0.3 | 0.3 | 0.3 | 0.3 | 0.3 | 0.3 |
| | Sorbic Acid | 0.2 | 0.2 | 0.2 | 0.2 | 0.2 | 0.2 |
| | Sodium Benzoate | 0.1 | 0.1 | 0.1 | 0.03 | | 0.1 |
| Emulsifier | | 0.2 | 0.01 | 0.01 | 0.5 | 0.5 | 0.01 |
| | Panodan | 0.2 | 0.01 | 0.01 | 0.5 | 0.5 | 0.01 |
| Lubricant | | 0.1 | 0.1 | 0.0 | 0.0 | 0.0 | 0.1 |
| | Lecithin Ultralec F | 0.1 | 0.1 | | | | 0.1 |
| Water | | 4.5 | 10.7 | 10.7 | 14.7 | 10.3 | 10.7 |
| Flavors | | 5.0 | 7.0 | 7.0 | 7.0 | 7.0 | 7.0 |
| | Meat Flavor | 5.0 | 5.0 | 5.0 | | | 5.0 |
| | Vegetarian Flavor | | 2.0 | 2.0 | | | 2.0 |
| | Fish/Poultry Flavor | | | | 7.0 | 7.0 | |
| Water Activity | | 0.653 @25.0 °C. | 0.668 @25.2 °C. | 0.554 @25.2 °C. | 0.681 @25.1 °C. | N/A | 0.680 @25.5 °C. |

The above ingredients are mixed at room temperature and then vacuum formed using the VERMAG machine noted above. Runs F, I, J were manufactured by creating a pre-emulsion of the mineral oil and the emulsifier. Separately, the dry mix was mixed for 2-3 minutes, and the water was then added slowly to the dry mix, and mixed into the batch for at least three more minutes to form a first wet intermediate. The pre-emulsion was then blended with the first wet intermediate and mixed for at least three minutes prior to being formed as final product. The final products have a dry, non-greasy appearance. Runs G, H, K were not made by adding a pre-emulsion to a wet mix, but rather by adding a stable emulsion of water, oil, and emulsifier to the dry ingredients. The result was a greasy product.

By the above examples and Tables 1 & 2 it is apparent that foodstuffs containing beneficial microorganisms and nutritionally important fatty acids may be provided in a chewable, storable form by the subject invention. For active ingredients that are water sensitive such as live microorganisms, then the amount of humectant is increased, to depress the water activity level down to about 0.65 while maintaining the stability and texture of the resultant product. The samples had a hardness of about 7 lbs, based on the measurement system above using the digital force gauge.

EXAMPLE 3

A comparison of probiotic formula with and without added oil was conducted, showing that both formulations are suitable for the administration of probiotic ingredients.

| INGREDIENT | | L | M |
|---|---|---|---|
| Oil Component | | 0.0 | 4.0 |
| | Mineral Oil | 0.0 | 4.0 |
| Probiotic Component | | 6.0 | 6.0 |
| | Pimalac 454 | 6.0 | 6.0 |
| Starch Component | | 25.0 | 25.0 |
| | Pregel Corn Starch (Staley Mira Sperse 2000) | 6.0 | 6.0 |
| | Pregel Starch (Staley Mir-Gel 463) | 19.0 | 19.0 |
| Sugar Component | | 23.0 | 23.0 |
| | Dextrose | 8.0 | 8.0 |
| | Sucrose | 9.0 | 9.0 |
| | Corn Syrup | 6.0 | 6.0 |
| Humectant | | 11.0 | 11.0 |
| | Sorbitol | 11.0 | 11.0 |
| Extender/Bulking Agent | | 23.6 | 23.6 |
| | Rice Bran | 23.6 | 23.6 |
| Preservative | | 0.3 | 0.3 |
| | Sorbic Acid | 0.2 | 0.2 |
| | Sodium Benzoate | 0.1 | 0.1 |
| Lubricant | | 0.1 | 0.1 |
| | Lecithin Ultralec F | 0.1 | 0.1 |
| Water | | 9.0 | 5.0 |
| Flavors | | 2.0 | 2.0 |
| | Meat Flavor | 2.0 | 2.0 |
| Colony Forming Units Per Gram | | | |

| INGREDIENT | L | M |
|---|---|---|
| initial | $4.06 \times 10^6$ | $3.39 \times 10^6$ |
| after 1 month | $4.06 \times 10^6$ | $3.04 \times 10^6$ |
| after 2 months | $1.67 \times 10^6$ | $1.31 \times 10^6$ |

The above ingredients are mixed at room temperature and then vacuum formed using the VERMAG machine noted above. The oil-containing run was manufactured by creating a pre-emulsion of the mineral oil and the emulsifier as in Example 2. The final product had a dry, non-greasy appearance.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments and equivalents falling within the scope of the appended claims.

I claim:

1. A composition for the oral administration of probiotics in a discrete dosage form, said discrete dosage form comprising:
    said probiotics consisting essentially of beneficial microorganisms included in a product at 0.1% to 30% by weight of the total product;
    the product further comprising 10% to 50% of a pregelatinized starch component, 25% to 50% sugar component, 0-20% humectant, and 5% to 25% water, by weight of the total product,
    wherein said product has a soft and chewy texture and a water activity of 0.60 to 0.75, and wherein said product does not contain fat or oil.

2. The composition of claim 1, wherein the water content is 10% by weight of the total product.

3. The composition of claim 1, wherein the humectant is a polyhydric alcohol, and the humectant content is 9% to 11% by weight of the total product.

4. The composition of claim 1, wherein the pregelatinized starch component is 25% to 35% by weight of the total product.

5. The composition of claim 1, wherein said product has a hardness of 7 to 33 pounds.

6. The composition of claim 1, wherein the water activity is 0.65.

7. The composition of claim 3, wherein the polyhydric alcohol is sorbitol.

8. The composition of claim 1, wherein the sugar content is 23-37% by weight of the total product.

9. The composition of claim 1, further comprising pharmaceutically effective amounts of ivermectin and pyrantel.

* * * * *